United States Patent [19]

Ehrlich

[11] Patent Number: 4,462,405
[45] Date of Patent: Jul. 31, 1984

[54] BLOOD LETTING APPARATUS

[76] Inventor: Joseph C. Ehrlich, 2440 Sedgewick Ave., Bronx, N.Y. 10468

[21] Appl. No.: 424,045

[22] Filed: Sep. 27, 1982

[51] Int. Cl.³ .................. A61B 17/34; A61B 17/32
[52] U.S. Cl. ............................. 128/329 R; 128/314
[58] Field of Search ............. 128/329 R, 329 A, 314, 128/315, 316; 604/93, 156, 157

[56] References Cited

U.S. PATENT DOCUMENTS

| 854,956 | 5/1907 | Martin | 128/329 R |
|---|---|---|---|
| 2,593,110 | 4/1952 | Crane et al. | 128/329 R |
| 3,030,959 | 4/1962 | Grünert | 128/329 R |
| 3,046,987 | 7/1962 | Ehrlich | 128/329 R |
| 3,086,530 | 4/1963 | Groom | 128/329 R |
| 3,208,452 | 9/1965 | Stern | 128/329 R |
| 3,338,239 | 8/1967 | Mausteller | 128/329 R |
| 3,358,689 | 12/1967 | Higgins | 128/329 R |
| 3,741,197 | 6/1973 | Sanz et al. | 128/314 |
| 4,139,011 | 2/1979 | Benoit et al. | 128/329 R |
| 4,203,446 | 5/1980 | Höfert et al. | 128/329 R |
| 4,379,456 | 4/1983 | Cornell et al. | 128/314 |

FOREIGN PATENT DOCUMENTS

| 84266 | 12/1894 | Fed. Rep. of Germany | 128/329 |
|---|---|---|---|
| 95452 | 2/1897 | Fed. Rep. of Germany | 128/329 R |
| 2405342 | 8/1975 | Fed. Rep. of Germany | 128/329 A |
| 949989 | 9/1949 | France | 128/329 R |
| 993499 | 10/1951 | France | 128/329 |
| 124247 | 3/1949 | Sweden | 128/314 |

Primary Examiner—C. Fred Rosenbaum
Assistant Examiner—C. W. Shedd
Attorney, Agent, or Firm—Mark T. Basseches; Paula T. Basseches

[57] ABSTRACT

Blood letting apparatus is disclosed which is particularly adapted for operation by the patient, the device being characterized by a substantial reduction in the pain of administration and by the provision of an efficient release of blood with minimal admixture of tissue fluids. A feature of the invention resides in the provision of a lancet carrier for removably receiving disposable sterile lancets and a hammer member for activating the carrier, the carrier being free of connection with the hammer whereby the point of the lancet may be disposed against the skin of the user in advance of the carrier being struck by the hammer.

9 Claims, 5 Drawing Figures

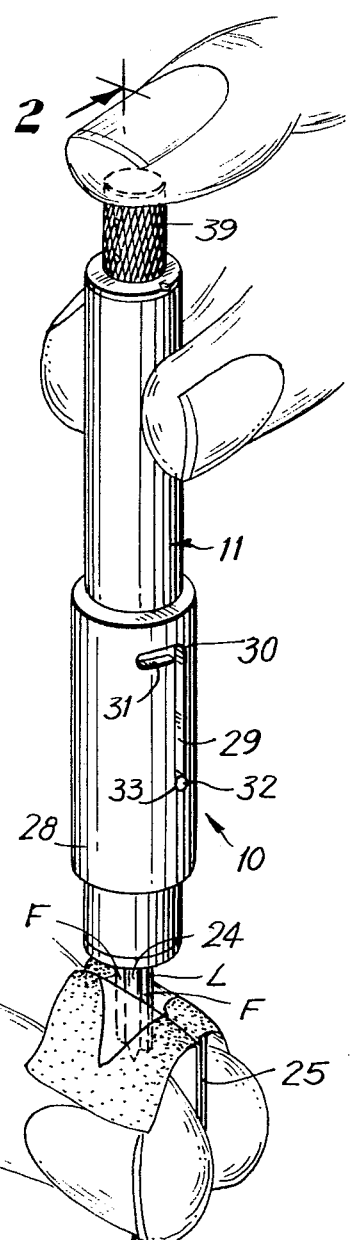
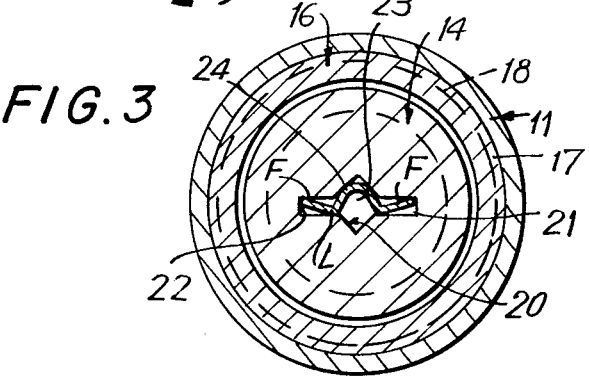
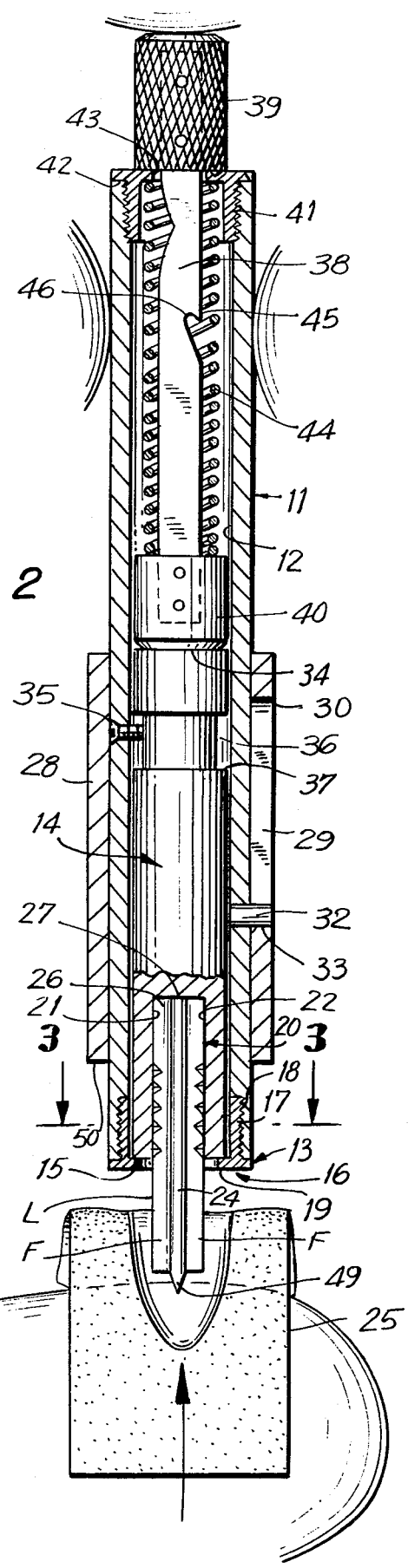

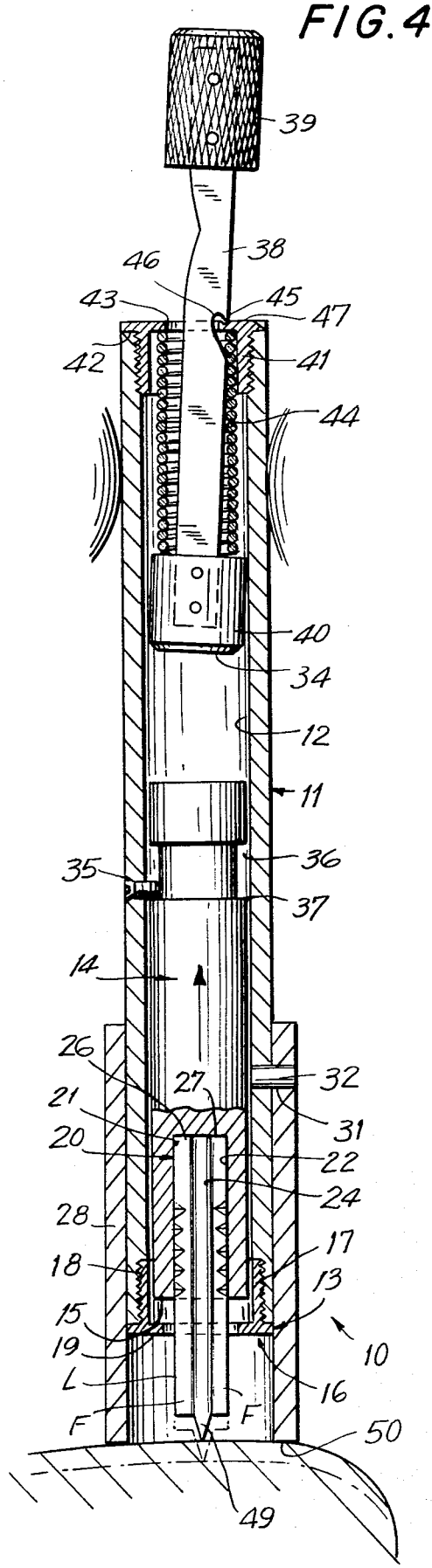
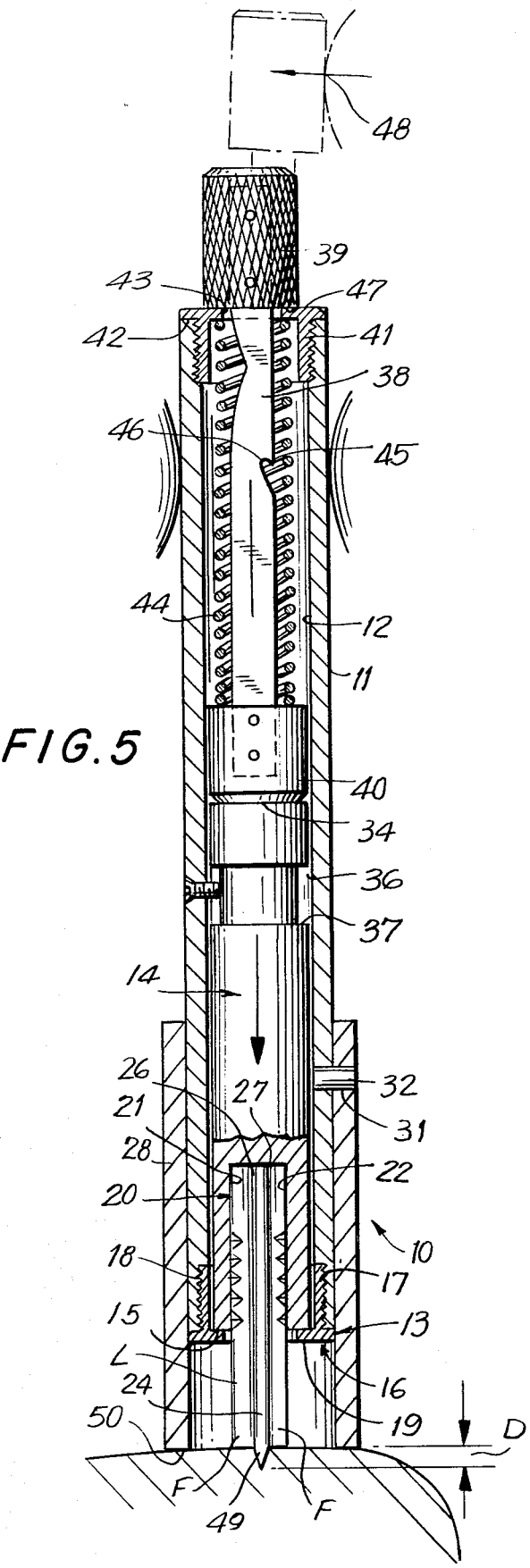

BLOOD LETTING APPARATUS

BACKGROUND OF THE INVENTION

1. Field of the Invention

The present invention resides in the field of a medical apparatus, and more particularly to a blood letting apparatus adapted for self-administration.

Some medical conditions, by way of example diabetes, require that the patient be tested for blood content, and particularly blood sugar content. In the case of a diabetic patient, at the early stages of insulin therapy it is necessary, in order to determine the proper insulin dosages, that blood samples be tested many times a day.

Numerous systems for patient self-monitoring of blood glucose levels have been developed. However, in each such system it is necessary for the patient or for an attendant to draw blood.

2. The Prior Art

Numerous devices have been employed for the drawing of the small quantities of blood necessary for effecting blood glucose level testing.

In my U.S. Pat. Nos. 2,801,633 and 3,046,987 there are disclosed various forms of an improved lancet member which enable the drawing of blood samples with minimal trauma to the patient and minimal admixture of tissue fluids, which latter tend prematurely to coagulate the blood and by admixing with the blood to give misleading or inaccurate readings.

The procedure of self blood letting by stabbing with a lancet or like piercing instrument, even using the improved lancets described in my above mentioned patents, presents a difficult task to the patient. There is a natural tendency for the patient to flinch, with the result that the desired clean wound will not be produced or that the lancet will not enter the skin in a perpendicular orientation. In addition, it is not unusual for an inexperienced patient to fail to insert the lancet through the dermal layers, with the result that the procedure must be repeated.

In order to minimize the manipulative procedures involved in a self-stabbing procedure, mechanical devices have been constructed which perform the stabbing task. Such devices typically employ a spring biased plunger which carries a sharpened end. The devices are used by cocking the plunger and positioning the distal portion of the device against the skin to be pierced, following which the plunger is released. The plunger will carry the lancet tip to a preset depth into the tissue of the patient.

The use of the devices of the type described has been found to be painful and to induce substantial trauma in the areas surrounding the puncture. It has been theorized that the trauma and pain are engendered in large measure by the speed at which the lancet is travelling when the wound is effected.

SUMMARY OF THE INVENTION

The present invention may be summarized as directed to a novel blood letting device which is characterized by simplicity of operation, assurance of sterility, predictability of depth of penetration, reduced trauma in surrounding tissues and, above all, minimization of pain sensation.

The apparatus includes a guide member within which is movably mounted a lancet carrier adapted to receive a sterile, disposable lancet. A hammer member is shiftable between cocked and fired positions. An important feature of the invention resides in the fact that the lancet carrier and hammer are independently movable.

In use, a lancet affixed in the carrier is positioned with its point resting on the surface of the skin, usually of a finger tip. The patient will thus perceive a slight pressure sensation from the point of the lancet itself. When the hammer is released from the cocked to the fired position, it strikes the carrier, whereby the cutting point of the lancet is forced into the tissue to a precisely predetermined depth.

It has unexpectedly been discovered that the sensation of pain is substantially lessened where there is initial contact between the lancet tip and the skin than is the case in conventional mechanical blood letting devices where the lancet point is brought from a position clear of the skin into forceable contact with and penetration of the skin.

It has further been found that the trauma produced by the described apparatus is substantially less than that experienced with manually or mechanically operated lancets heretofore known.

It is accordingly an object of the present invention to provide a blood letting device particularly adapted for self administration but, of course, also useful professionally, which is characterized by the assured provision of a clean and relatively painless wound, yielding blood samples containing a minimum of tissue fluids.

A further object of the invention is the provision of a device of the type described wherein a pouting or distending influence is exerted on the skin by the instrument, encouraging a free flow of blood.

Still a further object of the invention is the provision of a blood letting device of the type described having a mechanical hammer and a lancet carrier and wherein the carrier is independent of the hammer, whereby an initial pressure of the lancet against the skin is effected prior to release of the hammer, which sequence has been found greatly to reduce the pain factor in the blood letting process.

Still a further object of the invention is the provision of a device of the type described which is particularly well adapted to the use of lancets as disclosed in my U.S. Pat. Nos. 2,801,633 and 3,046,987.

To attain these objects and such further objects as may appear herein or be hereinafter pointed out, reference is made to the accompanying drawings forming a part hereof, in which:

FIG. 1 is a perspective view of a representative example of apparatus of the type described in the lancet loading position thereof;

FIG. 2 is a magnified vertical section taken on the line 2—2 of FIG. 1;

FIG. 3 is a further magnified horizontal section taken on the line 3—3 of FIG. 2;

FIGS. 4 and 5 are vertical sections similar to FIG. 2 showing the position of the parts, respectively in the prefired and fired positions thereof.

Referring now to the drawings, there is shown a blood letting instrument 10 which is comprised of a body portion or guide member 11, illustratively in the form of a hollow tube having an axially extending interior bore 12. Within the bore 12 and adjacent the bottom end 13 of the guide member 11 there is mounted an axially moveable lancet carrier member 14.

The carrier member 14 which, as seen in FIG. 3, is cylindrical in transverse section, includes an end portion 15 which is positioned to engage against a stop shoulder portion formed on bushing 16, the bushing having a threaded shank 17 engaging internal threads 18 in the guide member 11.

The bushing includes an inwardly directed annular stop shoulder portion 19 which limits downward movement of the carrier 14 by engagement with the shoulder or end 15 of the carrier.

The carrier 14 includes an axially directed channel, socket or chuck portion 20. The cross-sectional configuration of the portion 20 is shaped in conformity with the cross-section of the lancet intended to be utilized. In the illustrated embodiment, the channel 20 includes a pair of radially extending wings 21, 22 and a squared central portion 23. This shape of channel is especially adapted to receive a lancet L of the type shown, for instance, in FIG. 2 of my above referenced U.S. Pat. No. 3,046,987. Such lancets are commercially available under the trademark MICROLANCE and are manufactured by Becton, Dickinson & Co. of Rutherford, N.J.

As will best be seen from FIG. 3, the lancet is comprised of a very thin, flexible metallic member which, in transverse section, includes laterally directed flanges F which nest within the wings 21, 22 and an arched or arcuate center portion 24 which may be nested within the squared central portion 23 of the channel 20.

The lancet L may be inserted into the channel 20 in either of two positions offset from each other by 180° and by virtue of the transverse flexibility and interfit of the parts which result in a slight transverse distortion of the lancet in the course of insertion, will be frictionally retained within the chuck 20.

It will be readily recognized that the nature of the chuck may be conformed to the characteristics of the lancet to be employed and that movable spring jaws or other damping means may be embodied in the chuck to provide a gripping function.

As shown in FIG. 1, the lancet L is supplied in sterile condition in a wrapper 25, the lancet being mounted in the device by stripping the wrapper and forcing the upper end 26 of the lancet into the channel 20 until the upper end engages against stop shoulder 27 defining the uppermost end of the channel.

The guide member is provided with a collar 28 which surrounds the body thereof adjacent the lower end 13 and which is axially shiftable relative to the guide member between a retracted or loading position shown in FIGS. 1 and 2 and a gauging or operative position shown in FIGS. 4 and 5. More specifically, the collar 28 comprises a tubular section having an axially extending groove 29 formed therein, the upper end 30 of the groove having an arcuate slot 31. A locator pin 32 projects laterally from the body of the guide member and rides within the slot defined by portions 29 and 31.

As will be seen from FIGS. 1 and 2, when the collar 28 is lifted such that pin 32 is at the lower end 33 of the slot 29, the lower end of the carrier member is accessible adjacent the bottom 13 of the guide. In this position, as shown in FIG. 1, the lancet L may be readily inserted into the socket 20. Upward forces exerted in the course of insertion of the lancet are resisted by the hammer assembly, next to be described, which rests against the uppermost end 34 of the carrier 14.

Preferably the travel of the carrier 14 within the bore 12 of the guide member 11 is limited by a set screw 35 extending through the wall of the guide member 11 and into an annular groove 36 formed in the carrier member adjacent the upper end thereof.

As will be seen, the groove 36 includes a lower shoulder 37 which, when upward forces are exerted against the carrier, will engage against set screw 35 to preclude further lifting movements of the carrier.

As previously noted, downward movement of the carrier beyond the lower end 13 of the guide member 11 is governed by engagement of the lowermost end 15 of the carrier and the annular shoulder 19 of bushing 16.

The hammer assembly comprises a drive rod 38 having a knurled lifter 39 at its upper end and an impact head 40 at its lower end. A top bushing member 41 is threadedly secured in the upper end 42 of the guide member, the bushing including a transverse slot 43 slidably guiding the drive rod 38. A recoil spring 44 is biased between the bushing 41 and the impact head 40 and normally urges the head to its downward position shown in FIGS. 1, 2 and 5.

The rod 38, which is tiltable relative to slot 43, includes a detent tooth 45 and an adjacent recess 46. As will be seen from FIG. 4, the hammer may be cocked by withdrawing or upwardly shifting the knob 39 and tilting the rod 38 such that the tooth 45 engages the retainer shoulder 47 by resting in recess 46.

As will be apparent, firing of the device, i.e. shifting of the hammer assembly from the position shown in FIG. 4 to that shown in FIG. 5, is effected by tilting the knob 39, which acts as a trigger, in the direction of the arrow 48, FIG. 5.

The operation of the device will be appparent from the preceding description.

A lancet member L is loaded into the chuck 20 with the parts positioned as shown in FIGS. 1 and 2, with the hammer assembly in the fired position and with the collar 28 in its uppermost or loading position. Thereafter, the collar 28 is shifted downwardly to its operating or gauging position by sliding the collar such that the pin 32 rides to the upper end 30 of groove 29 and thereafter rotating the collar such that the pin rides in the arcuate slot or groove portion 31.

The hammer assembly is cocked by withdrawing the knob 39, seating the tooth 45 on the retainer shoulder 47 with its point resting in recess 46, as shown in FIG. 4. In this position the tip 49 of the lancet may project a distance below the lowermost or gauging end 50 of the collar 28 (see dotted line position, FIG. 4). The distance of such projection is calculated to lie in a preferred range of from about 1 to 3 mm.

The apparatus is next placed against the sterilized skin of the patient, illustratively against a finger tip, the hand preferably resting on a stable surface, such as a table or the like so as to prevent the finger from recoiling.

As will be seen from FIG. 4, the action of pressing the gauging end 50 against the finger will cause the carrier, by pressure of the finger against the lancet tip, to be lifted within the bore 12 from the dotted to the solid line position shown in FIG. 4. This lifting action is resisted at least slightly by the frictional interfit of the carrier in bore 12, or by the weight of the carrier and lancet.

The device is triggered by shifting the knob 39 laterally, releasing the tooth 45 of drive rod 38 from the recess 46 and edge of the bushing 41. The rod is free to move abruptly downward through the bushing slot 43 by the sudden expansion of the recoil spring 44, whereupon the impact head 40 of the hammer assembly will forcibly strike the upper surface 34 of the carrier, driving the carrier member downwardly toward the finger until the end 15 of the carrier engages against the stop shoulder 19, resting in the point 49 of the lancet being driven a distance D (FIG. 5) through the skin of the patient. The distance D is, as noted, within the specified range from about 1 to 3 mm.

Where the selected lancet is of the type shown in my above referenced patents, the depth of penetration is controlled not only by the throw of the carrier member but also by the shoulder portions of the lancet surrounding the point 49 which limit the maximum depth of penetration to 2 mm. The significance of such double depth penetration control is that portions of the finger may bulge upwardly into the collar if the instrument is pressed against the finger with undue downward force. Thus, the shoulders of the preferred form of lancet act as a secondary protection in the event of improper manipulation of the instrument.

The collar exerts a spreading force on the portion of the finger which it surrounds and promotes bleeding.

From the foregoing it will be appreciated that there is described a blood letting instrument which may readily be employed in conjunction with disposable lancet members.

As noted, the sensation of pain is substantially reduced by the fact that the cutting tip of the lancet is in actual and perferably slightly pressured contact with the skin at the onset of impact of the hammer against the carrier.

Additionally, I have discovered that by having an initial contact between lancet tip and skin, the lancet tip enters the dermis with a cutting action rather than a bruising action. Thus, in addition to minimizing trauma, the pain receptors which are affected by the entry of the point into the skin are only those located at the margin of the incision. In contrast, the crushing action of a rapidly moving point affects a wider zone of pain receptors.

Without limitation, the above noted theories may explain the reduced pain sensation achieved through the use of the instant device.

Preferably the interfit of the carrier in the bore of the guide member is such as to provide a slight resistance or frictional restraint on the relative movement of the carrier and guide member. If desired, means such as a resilient projecting member may be formed on the carrier or the carrier-adjacent surface of the guide to augment the described frictional force. By this means a significant pressure may be exerted by the lancet point against the skin of the user when the gauging end 50 of the collar is placed against the skin. This force should not be sufficient to effect penetration of the point but desirably should be sufficient to provide the user with the sensation of the presence of the point.

By separating the carrier mass from the hammer, it will be observed that lesser forces are required in effecting the incision.

Optionally, the hammer (or the upper end of the carrier) may be padded with rubber so as to reduce the sound of impact, it being observed that a silent operation is preferable since the anxiety factor of the user is increased where a loud noise accompanies the formation of the incision.

As will be apparent to those skilled in the art and familiarized with the instant disclosure, numerous variations in details of construction may be made from those of the illustrated embodiment. Accordingly, the invention is to be broadly construed within the scope of the appended claims.

Having thus described the invention and illustrated its use, what is claimed as new and is desired to be secured by Letters Patent is:

1. A blood letting apparatus comprising a guide member having an internal bore, a hammer movably mounted in one end of said bore, said hammer being shiftable axially between cocked and fired positions, spring means reacting between said guide member and hammer and urging said hammer toward said fired position, a lancet carrier member movably mounted in said bore adjacent the other end of said guide member, said carrier member being free of connection to and movable independently of said hammer, said carrier member including a chuck portion directed toward said other end of said guide member, a lancet adapted to be frictionally retained in said guide member, stop means on said guide member in the path of said carrier member for limiting outward axial movement of said carrier member relative to said other end, and a tubular collar member axially movably mounted on said guide member, said collar member being shiftable between a retracted loading position and a projected gauging position, said collar member, in said gauging position including a free end portion extending a predetermined distance beyond said other end of said guide member, said lancet, in said gauging position of said collar member, being positioned relative to said free end portion of said collar member to exert a finite pressure against the skin of the patient.

2. Apparatus in accordance with claim 1 wherein said hammer, in the cocked position thereof, is spaced from said carrier member, the combination including trigger means actuable to shift said hammer into impacting engagement with said carrier member, thereby to urge said carrier member against said stop means.

3. Apparatus in accordance with claim 2 wherein said chuck comprises an axially directed passage formed in said carrier member and said lancet comprises a transversely deformable metallic member cross-sectioned to be frictionally retained in deformed condition in said passage.

4. Apparatus in accordance with claim 2 wherein said lancet includes a sharpened tip portion, said tip portion projecting from 1 to 3 millimeters beyond said free end portion of said collar member when said collar member is in the gauging position thereof and said carrier member is engaged against said stop means.

5. Apparatus in accordance with claim 2 and including limit means interposed between said guide and carrier members for restricting movement of said carrier member in a direction away from said other end.

6. Apparatus in accordance with claim 1 and including limit means interposed between said guide and carrier members for restricting movement of said carrier member in a direction away from said other end.

7. Apparatus in accordance with claim 1 wherein said carrier member is yieldably resistant to movement away from said other end.

8. A blood letting apparatus comprising a guide member having an internal bore, a hammer mounted adjacent one end of said guide member and shiftable toward and away from the other end of said guide member between fired and cocked limiting positions, respectively, spring means urging said hammer toward said fired position, trigger means for shifting said hammer from said cocked to said fired position, a lancet carrier member axially moveably mounted in said bore adjacent said other end, said carrier member including a chuck means directed outwardly of said other end, said carrier member being free of connection with and independently movable relative to said hammer, a replaceable lancet adapted to be inserted through said other end into said chuck means, said lancet including a piercing tip, stop means on said guide member in the path of said carrier member for limiting movement of said carrier member in the direction of said other end, and depth gauge means on said other end of said guide member and defining a free end thereof, said tip projecting a predetermined distance beyond said free end of said depth gauge means when said carrier member is engaged against said stop means, said carrier member being yieldably resistant to movement away from said other end whereby, when said free end of said depth gauge is pressed against the skin of a patient, said carrier member is shifted within said guide member away from said other end, and said tip of said lancet is thereby disposed in pressured contact with the skin of the patient.

9. Apparatus in accordance with claim 8 wherein said trigger means comprises a drive rod connected to said hammer and shiftable transversely relative to said guide member, a tooth on said drive rod, a shoulder formed on said guide member and adapted to receive said tooth when said hammer is shifted toward said one end transversely relative to said guide member, said trigger means being released responsive to transverse movement of said guide rod, thereby to clear said tooth from said shoulder.

* * * * *